United States Patent [19]

McBrayer

[11] 4,442,092

[45] Apr. 10, 1984

[54] SESAME NEMATOCIDAL COMPOSITION

[76] Inventor: Bob W. McBrayer, P.O. Box 128, Dixon, Calif. 95620

[21] Appl. No.: 369,623

[22] Filed: Apr. 19, 1982

[51] Int. Cl.$^3$ .............................................. A61K 35/78
[52] U.S. Cl. ...................................................... 424/195
[58] Field of Search ........................ 424/195; 424/194

[56] References Cited

U.S. PATENT DOCUMENTS

| | | | |
|---|---|---|---|
| 2,202,145 | 5/1940 | Eagleson | 424/189 |
| 2,463,324 | 3/1949 | Simanton | 424/189 |
| 2,786,063 | 3/1957 | Purdy et al. | 549/439 |
| 2,832,792 | 4/1958 | Besoza | 424/188 |

OTHER PUBLICATIONS

Budowski et al., Chem. Revs. 48, 125 (1951), p. 141.
Webster's 7th New Collegiate Dictonary G & C Merrion Co. p. 793, Sesame 1963.
The Merck Index 9th ed., Sesame 8214, 1976.
Budowski et al The Chemical and Physiological properties of Sesame oil Chem rev. 48125 (1951) p. 141.

*Primary Examiner*—Albert T. Meyers
*Assistant Examiner*—John W. Rollens, Sr.
*Attorney, Agent, or Firm*—Harry A. Pacini

[57] ABSTRACT

A nematocidal composition containing as an active ingredient(s) therein sesame plant extracts including roots, seeds or stalks, oils and acids extracted therefrom, but primarily sesamin, sesamolin and sesamol.

10 Claims, No Drawings

SESAME NEMATOCIDAL COMPOSITION

This invention relates to a nematocidal compositions containing sesame seeds, sesame seed extracts, sesame plants, or oils and acids extracted therefrom as the active ingredient or ingredients.

DESCRIPTION OF THE PRIOR ART

In areas where upland farming is the general practice of agriculture, damage of the annual or perennial plants by the injurious soil nematodes, such as root knot nematodes, root-lesion nematodes and cyst nematodes are a large problem. Agronomists and biologists are continuing to labor to find effective methods of control for such injurious soil nematodes. Development of safe and effective nematocidal compositions is a desirable achievement.

Heretofore, a number of different kinds of nematocides have been developed and practically used for controlling of said injurious soil nematodes. In use, most of these nematocides are diffused into the soil in the form of a gas to kill the nematodes which come into contact with the diffused gas. Among of them, typical compounds used for such nematocides are, for example, EDB (1,2-dibromoethane), D-D (1,3-dichloropropene and 1,2-dichloropropane), chloropicrin (trichloronitromethane), methyl bromide, carbam (ammonium or sodium N-methyl-dithiocarbamate), DCIP (bis-(2-chloro-1-methylethyl)ether) and DBCP (1,2-dibromo-3-chloropropane). These compounds can be gasified at a normal temperature and easily diffused into the soil, so that they produce a relatively high killing effect against the injurious soil pests. On the other hand, because of their strong toxicity, inflammability and irritative action, their use in the neighborhood of cities is attended by many problems, and certain restrictions are imposed on their storage and use. Also, damage to crops from these chemicals can be extensive and no planting is allowed unless the gaseous compounds diffused in the soil are eliminated. Further, because of their non-specific killing effect against the living things in the soil, these compounds might annihilate even the usefull organisms living in the soil, and if the injurious soil nematodes are given a chance to again invade to the once treated soil, the density of such nematodes will increase in such soil rapidly, and on the second year after planting, even a greater degree of damage may be caused than in the non-treated soil.

DESCRIPTION OF THE INVENTION

The present invention does not employ chemical compounds which are synthesized or otherwise foreign to nature. The present invention arises from a study of compositions effective for controlling the injurious soil nematodes and the finding that certain compositions derived from sesame plants have a specific, heretofore unknown, killing or controlling action against such soil nematodes. The invention was completed on the basis of such findings.

There are many natural occurring materials which are known effective as herbicides or insecticides. There are many favorable reasons to employ a natural occurring product in the control of undesirable organisms such as soil nematodes. Natural decomposition in the soil and non-injuring to high life forms rank among the most noteworthy. Hence, the use of compositions derived from the sesame plant falls into this category of beneficial, economic and environmental considerations.

Sesame is from the generic Sesamum, a member of the Pedaliaceae family. The plant is grown primarily for its seed and oil expressed therefrom. Sesame oil is from sesame seed, of the cultivated *S. indicum*. There are in addition about seventeen wild species reported as occurring in Africa and two in India. *S. indicum* is an herbaceous plant growing several feet high with a vegetative cycle of only 3 or 4 months. Sesame is one of the highes-yielding, non-perennial oil plants.

Sesame oil is reported as a synergist with certain insecticides - U.S. Pat. No. 2,202,145 (May 28, 1940); U.S. Pat. No. 2,463,324 (Mar. 1, 1949). The latter Patent discloses that sesame oil contains a material which is a synergist for certain insecticides, such as pyrethrum.

Sesame oil, meal and extracts of the sesame plant have been found to contain a mixture of unsaponifiable materials such or sesamin, sesamolin and sesamol. The specific nematocidal activity noted and forming the basis of the present application may not be assigned to any particular constituent of the sesame plant, oil or other derivable portion therefrom. There is no reason to doubt that the constituent of either sesame oil or the sesame plant chiefly responsible for the nematocidal activity herein noted, is a complex of factors which according to the composition of the plant or any extract therefrom, may cause the nematocidal activity.

Therefore, it is the present invention to provide a composition effective against nematocides in which the active ingredient is derived from the sesame plant, in the form of an extract of the plant, seeds, roots or ground solid meal of said parts of the sesame plant or total plant. There is provided a nematocial composition which is non-phytoxic, non-toxic to humans or high life forms.

There is no synthesis of the active ingredient rather the active ingredient is derived from the natural grown sesame plant. As will be illustrated hereafter, extraction of the plant is possible, however, the entire plant may be used in toto. The following examples illustrate the use of the present invention to control nematodes.

METHOD OF USE - TO CONTROL NEMATODES APPLICATION a. SUITABLE AGRICULTURAL FORMULATIONS

The compositions disclosed herein may themselves be applied directly to the area where the deleterious effects of the plant pests are to be controlled. It is, however, preferable to use suitable agricultural formulations which contain other ingredients which enhance application of the compositions. These agricultural formulations will generally comprise about 5 percent to 95 percent or more by weight of one or more nematocidally active sesame oil, meal, or extracts disclosed herein, or mixtures of these compositions and either from 1 percent to 95 percent by weight of an agricultural diluent, or from 1 percent to 20 percent by weight of a surface active agent and other ingredients required to produce wettable powders, dusts, solutions, emulsifiable concentrates, granules, and the like, or both.

Wettable powders will contain from 25 to 80 percent active ingredients from 0.1 percent to 5.0 percent wetters and dispersants with the balance consisting of inorganic absorptive diluents.

Since some compounds are solids, others are liquids, and others are viscous materials, they may be dissolved in one or more solvents and then sprayed upon the absorptive diluents of attapulgite clay, synthetic fine silica, and synthetic calcium and sodium alumino-silicates, or other solid insecticides, or foliar fungicides mentioned herein and then the solvent or solvents are evaporated off.

Emulsifiable oils will contain from 20 percent to 97 percent active ingredient, from 3.0 to 10.0 percent of an emulsifying agent, and may also contain from 1 percent to 77 percent water-immiscible solvent such as xylene or alkylate naphthalene.

Granules will contain from 5 percent to 25 percent active ingredient, and may also contain from 1 percent to 20 percent of a surfactant extended upon a granular base such as vermiculite or granular attapulgite. Granules produced by extrusion or tumbling will contain like amounts of active ingredient and surfactant.

b. COMBINATION WITH OTHER INSECTICIDES AND FUNGICIDES

For the control of a wider range of crop-pests and diseases it is sometimes desirable to combine one or more nematocidally active sesame oil, meal or extracts with from 0.05 to 4 parts by weight of insecticides and fungicides, etc., known to be effective against crop-pests and diseases in concentrated premix or during the application step for foliar applications. Examples of other pesticides are: Sevin 1(naphthyl-N-methylcarbamate), Chlorobenzilate (ethyl 4,4'-dichlorobenzilate), Guthion (0,0-diethyl-S-(4-oxo-1,2,3,-benzotriazin-3(4H)-ylmethyl) phosphorodithioate), Disyston (0,0-diethyl-S-(2-(ethylsulfinyl)ethyl)phosphorodithioate), Maneb (manganous ethylene bisdithiocarbamate), Karathane (mixture of 2,4-dinitro-6-octylphenylcrotonate, 2,6-dinitro-4-octylphenylcrotonate, nitrooctylphenols (principally dinitro),4-(1-methylheptyl)2,6-dinitrophenylcrotonate, 4-(1-ethylhexyl)2,6-dinitrophenylcrotonate, 4-(1-propylpentyl)-2,6-dinitrophenylcrotonate, 6-(1-methylheptyl)-2,4-dinitrophenylcrotonate, 6-(1-ethylhexyl)2,4-dinitrophenylcrotonate, and 6-(1-propylpentyl)2,4-dinitrophenylcrotonate), Blasticidin (blasticidin-S-benzylaminobenzenesulfonate), Benlate (methyl 1-(butylcarbamoyl)-2-benzimidazolecarbamate), or Plantvax (5,6-dihydro-2-methyl-1,4-oxathiin-3-carboxanilide-4,4-dioxide).

In some instances it is also desirable to include special purpose additives which will inhibit corrosion reduce foaming, reduce caking, or increase flocculation.

The following example illustrates a suitable emulsifiable concentrate formulation, for dilution in water for spraying plants, particularly, plant foliage or for application to other plant parts as herein mentioned. In this emulsifiable concentrate formulation, the percentages are weight percent.

EXAMPLE

Emulsifiable Concentrate Formulations

| Sesame oil, meal or extract | 35% |
|---|---|
| Xylene | 30% |
| Isophorone | 30% |
| Atlox (R) 3404* | 1% |
| Atlox (R) 3403 F* | 4% |

* Commercial emulsifier for agricultural pesticides manufactured by Atlas Powder Co., Wilmington Delaware, and registered with the U.S. Food and Drug Administration.

c. AMOUNT OF SESAME MATERIAL DESCRIBED HEREIN TO APPLY

The nematocidally active compositions contains sesame oil, sesame meal, or sesame plant extracts are applied in an amount to be effective to control the nematode infestation i.e. a nematocidally effective amount. This amount is a nematocidally effective amount, which amount will vary with the season of the year, the weather, the severity of its infestation, the nematode pests include those specifically described and shown herein as well or equivalent species which are biologically related. For example, those nematode species of the geneae Meloidogyne, Heterodera, Xiphinema and the others may be controlled by application of the compositions.

Other species of nematodes may be controlled by applications other than by systemic foliage contract, for example, by supplying the compositions having activity against the harmful effects of nematodes to the soil, or by dipping the bulbs in solutions. Some examples of these other nematodes are:

| | |
|---|---|
| Aphelenchoides species | Bud and Leaf Nematodes |
| Anguina tritici | Wheat Nematode |
| Auguina agrostis | Grass Nematode |
| Belonolaimus species | String Nematodes |
| Criconemoides species | Ring Nematodes |
| Ditylonchus dipsaci | Stem and Bulb Nematode |
| Ditylonchus Potato Rot Nematode | |
| Ditylonchus angustus | Rice Nematode |
| Dolichodorus heterocephalus | Awl Nematode |
| Helicotylenchus species | Spiral Nematodes |
| Heterodera rostochiensis | Golden Nematode |
| Heterodera tabacum | Tabacco Cyst Nematode |
| Heterodera schachtii | Sugar Beet Nematode |
| Heterodera carotae | Carrot Root Nematode |
| Heterodera gottingiana | Pea Root Nematode |
| Heterdoera Soybean Cyst Nematode | |
| Hoplolaimus species | Lance Nematodes |
| Pratylenchus brachyurus | Smooth-headed Lesion Nematode |
| Pratylenchus species | Meadow Nematodes |
| Pratylenchus musicola | Banana Nematode |
| Pratylenchus Zeae | Corn Nematode |
| Radopholus similis | Burrowing Nematode |
| Rotylenchus reniformis | Kidney-shaped Nematode |
| Trichodorus species | Stubby-root Nematodes |
| Tylenchlorhynchus claytoni | Tobacco Stunt Nematode |
| Xiphinema species | Dagger Nematodes |

When used to control the soil nematodes the novel compositions may be applied at rates of from 6 pounds per acre per 6 inch depth of soil to as high as 500 pounds per acre per 6 inch depth of soil, depending upon, the application method, e.g., soil incorporation, discing, band, the type of formulation used, the plant species to be protected, the extend of the soil infestation, local conditions such as temperature, humidity, moisture content of the soil, nature of the soil, e.g., clay, loam, sand, pH, etc.

The present sesame compositions may be used at rates such as from 6 pounds per acre to 300 pounds per acre, or at lower rates of 12 pounds per acre to 200 pounds per acre, or optionally at the lowest rates of 12 pounds per acre to 50 pounds per acre. Also rates at 50 parts per million to 5,000 parts per million may be used.

The phrase "to effectively control the deleterious effects of plant pest" as used herein and in the claims means that control required to increase the yield of plants growing in infested areas and treated with the sesame compositions, as compared to non-treated plants. This effective control may range from 10 percent to 100 percent control.

The phrase "applying a nematocidally effective amount" as used herein and in the claims means applying that amount necessary to attain effective control by any application technique in which the compound and plant pest are brought into mutual contact, such as to the foliage of the plant, to the soil itself, to the nematode itself, or other plant pest.

TEST EXAMPLE I

Nematicidal activity on *Meloidogyne Incognita* (root knot Nematode), *Heterodera Schachtii* (Cyst nematode) and *Xiphinema Americanum* (Dagger Nematode).

The nematodes tested were of the groups of individuals, mostly larvae of the species of nematodes Meloidogyne, Heterodera and Xiphinema under indoor cultivation.

Total sesame plant was ground to meal, then was extracted with petroleum ether and/or ethanol. The extract was concentrated and used as the active ingredient in this in vitro test procedure. The above indentified nematode species were isolated. Soil, 5 grams, in 8 inch pots were inoculated in 6-part repetitions.

The active ingredient was applied to the inoculated soil at varing increments between 100 parts per million to 1000 parts per million and disced into the soil. The inoculated and treated pots with growing plants were placed in a green house and kept under greenhouse conditions for three months. The pots were planted with grape, tomato and sugarbeet plants.

The soil from each pot was then examined for dead and surviving nematodes to determine the mortality (% control). The rate of parasitic knots and the degree of phytotoxicity was observed. As stated above the test was carried out in a six part repetition. In summary, it was found that there was no phytotoxicity to the crop plants at any rate or concentration. Complete control of parasitic knots was observed at 500 parts per million (ppm) and higher concentrations. At lesser concentrations (less than 500 ppm) lesser control was observed. The rate of parasitic knots and lesions were expressed as light, moderate, heavy and severe.

As viewed above, the sesame compositions according to this invention show an excellent effectiveness against the root-lesion nematodes and root-knot nematodes which damage seriously to the principal farm products, while said sesame compositions are non-phytotoxic to the indicator plants.

While the invention has been descrived with reference to specific details of certain illustrative embodiments, it is not intended that it shall be limited thereby except insofar as such details appear in the accompanying claims.

What is claimed is:

1. A method for killing nematodes comprising treating soil infested with nematodes with a nematocidally effective amount of a composition containing as active nematocidal ingredients of at least one or more of the following total sesame plant meal or the extracts thereof or concentrate of the extract of the sesame plant meal.

2. A method according to claim 1 wherein the active nematocidal ingredient is the sesame plant meal.

3. A method according to claim 1 wherein the active nematocidal ingrediant is an extract of the sesame plant meal.

4. The method of effectively controlling the deleterious effect of the plant pest nematode occurring in soil by applying to said soil a non-phytotoxic nematocidally effective amount of a composition containing as the active ingredient at least one of the following: total sesame plant meal, the extracts, thereof or concentrate of the extract of the sesame plant meal.

5. The method of claim 4 wherein the active ingredient is essentially the sesame plant meal.

6. The method of claim 4 wherein the active ingredient is an extract of the sesame plant meal.

7. The method of claim 4 wherein the active ingredient is in the form of a wettable powder, dust, solutions, emulsifiable concentrate or granule.

8. The method of claim 7 wherein said form of active ingredient contains about 5 percent to about 95 percent by weight of said active ingredient.

9. The method of claim 8 wherein said form of active ingredient additionally contains from 1 percent to 20 percent by weight of a surface active agent or from 0.1 percent to 5.0 percent wetters and dispersents, or from 3.0 percent to about 10.0 percent of an emulsifying agent and from 1 percent to 77 percent water-immiscible solvent therefor.

10. The method of claim 8 wherein said form of active ingredient is from 5 percent to 25 percent and contains from 1 percent to 20 percent of a surfactant extended upon a granular base.

* * * * *